US010253380B2

(12) United States Patent
Mate De Gerando et al.

(10) Patent No.: US 10,253,380 B2
(45) Date of Patent: Apr. 9, 2019

(54) **MUTANT STRAINS OF THE GENUS *CLOSTRIDIUM BEIJERINCKII***

(71) Applicants: IFP Energies nouvelles, Rueil-Malmaison (FR); Stichting Wageningen Research, Wageningen (NL)

(72) Inventors: Hadrien-Felix Mate De Gerando, Paris (FR); Laetitia Rudant, Pompignac (FR); Marcel Ropars, Palaiseau (FR); Nicolas Lopes Ferreira, Croisilles (FR); Ana Maria Lopez Contreras, Utrecht (NL)

(73) Assignees: IFP Energies nouvelles, Rueil-Malmaison (FR); Stichting Wageningen Research, Wageningen (NL)

( * ) Notice: Subject to any disclaimer, the term of this patent is extended or adjusted under 35 U.S.C. 154(b) by 0 days.

(21) Appl. No.: 15/579,453

(22) PCT Filed: Apr. 1, 2016

(86) PCT No.: PCT/EP2016/057236
§ 371 (c)(1),
(2) Date: Dec. 4, 2017

(87) PCT Pub. No.: WO2016/192871
PCT Pub. Date: Dec. 8, 2016

(65) Prior Publication Data

US 2018/0142311 A1 May 24, 2018

(30) Foreign Application Priority Data

Jun. 4, 2015 (FR) ..................................... 15 55105
Dec. 10, 2015 (FR) ..................................... 15 62114

(51) Int. Cl.
*C12N 15/01* (2006.01)
*C12P 7/16* (2006.01)
*C12R 1/145* (2006.01)
*C12P 7/04* (2006.01)
*C12N 1/20* (2006.01)
*C12N 1/22* (2006.01)

(52) U.S. Cl.
CPC ................ *C12R 1/145* (2013.01); *C12N 1/20* (2013.01); *C12N 1/22* (2013.01); *C12N 15/01* (2013.01); *C12P 7/04* (2013.01); *C12P 7/16* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,216,820 | B2 | 7/2012 | Yukawa |
| 8,460,906 | B2 | 6/2013 | Contag |
| 2012/0301936 | A1 | 11/2012 | Lee |
| 2013/0149757 | A1 | 6/2013 | Day |
| 2015/0056168 | A1 | 2/2015 | Minton |

FOREIGN PATENT DOCUMENTS

| | | | |
|---|---|---|---|
| EP | 2270135 | A1 | 1/2011 |
| WO | 2009126795 | A2 | 10/2009 |
| WO | 2013086458 | A1 | 6/2013 |
| WO | 2013144647 | A1 | 10/2013 |

OTHER PUBLICATIONS

Prather et al. Curr Opin Biotechnol. Oct. 2008;19(5):468-74. (Year: 2008).*
International Search Report PCT/EP2016/057236 dated May 20, 2016.
H. Máté De Gérando et al: "Improving isopropanol tolerance and production of Clostridium beijerinckii DSM 6423 by random mutagenesis and genome shuffling", Applied Microbiology and Biotechnology, Feb. 6, 2016 (Feb. 6, 2016), DE, XP055271099, ISSN: 0175-7598.
Xiaofeng Gao et al: "Genome Shuffling ofCICC 8012 for Improved Production of Acetone-Butanol-Ethanol (ABE)", Current Microbiology, Springer-Verlag, NE, vol. 65, No. 2, May 6, 2012 (May 6, 2012), pp. 128-132, XP035074546, ISSN: 1432-0991.
Haifeng Su et al: "Development and application of a novel screening method and experimental use of the mutant bacterial strain Clostridium beijerinckii NCIMB 8052 for production of butanol via fermentation of fresh cassava", RSC Adv., vol. 5, No. 17, Jan. 15, 2015 (Jan. 15, 2015), pp. 12624-12637, XP055239553.
Shrikant A Survase et al: "Continuous production of isopropanol and butanol usingDSM 6423", Applied Microbiology and Biotechnology, Springer, Berlin, DE, vol. 91, No. 5, May 15, 2011 (May 15, 2011), pp. 1305-1313, XP019937220, ISSN: 1432-0614.

* cited by examiner

*Primary Examiner* — Christian L Fronda
(74) *Attorney, Agent, or Firm* — Millen, White, Zelano and Branigan, P.C.

(57) ABSTRACT

The present invention relates to mutant bacteria of the genus *Clostridium beijerinckii*, CNCM I-4985, CNCM I-4986, CNCM I-4987 and CNCM I-4988, deposited at the Institut Pasteur (CNCM, 25 rue du Docteur Roux, F-75724 PARIS Cedex 15, France) on 27 May 2015, and CNCM I-5027, CNCM I-5028 and CNCM I-5029 deposited at the Institut Pasteur (CNCM, 25 rue du Docteur Roux, F-75724 PARIS Cedex 15, France) on 26 Nov. 2015, which are useful in the fermentation of sugars for the production of isopropanol and butanol.

13 Claims, No Drawings

MUTANT STRAINS OF THE GENUS *CLOSTRIDIUM BEIJERINCKII*

The present invention relates to bacteria of the genus *Clostridium beijerinckii* improved by random mutagenesis as well as a process for the production of a mixture comprising butanol and isopropanol using these bacteria.

STATE OF THE ART

Many so-called "platform" chemical molecules composed of 2 to 6 carbon atoms are mainly produced from fossil resources. These base molecules are used for the production of intermediate compounds, the uses of which are varied, such as for example for the synthesis of polymers, of pharmaceutical molecules, in the formulations of fuels or also in the perfume industry.

However, for certain environmental reasons, but above all to address the inevitable decline in petroleum resources, alternative processes are being developed to allow the production of these "platform" molecules from renewable raw material.

Propylene (or propene) is the second most used molecule in petrochemistry. It mainly originates from petroleum and is in particular obtained by steam cracking, by catalytic cracking or by the dehydrogenation of propane.

One of the possible ways of producing propylene other than from petroleum is to carry out the dehydration of isopropanol obtained by biological fermentation of sugars extracted from biomass, a fermentation known as IBE (Isopropanol, Butanol, Ethanol) fermentation.

Fermentations called "solventogenic fermentation" are carried out by microorganisms of the genus *Clostridium*. Clostridia are Gram-positive bacilli capable of forming endospores and belonging to the phylum of the Firmicutes. These bacteria are strictly anaerobic and ubiquitous; they can be found in the intestines of animals, in soil etc. They can degrade different sugars and produce solvents from a wide variety of substrates. On completion of this "solventogenic" fermentation, the final products can vary according to whether the fermentation is of the ABE type (production of Acetone, Butanol and Ethanol) or of the IBE type (production of Isopropanol, Butanol and Ethanol).

The most studied "ABE" strain is *Clostridium acetobutylicum* ATCC 824, isolated from the soil in Connecticut in 1924 (Weyer & Rettger, 1927, J. Bacteriol. 14, 399-424). Another much-studied strain is *Clostridium beijerinckii* DSMZ 6423 (NRRL B593), because it is capable of producing a mix of Isopropanol/Butanol/Ethanol solvents by reducing acetone to isopropanol due to the presence in its genome of an NADPH-dependent primary/secondary alcohol dehydrogenase (adh) (Ismaiel et al., 1993, J. Bacteriol., 175(16), 5097-105).

The main constraint linked to the development of industrial processes for the production of solvents by strains of *Clostridium* is the final solvents titre, a problem which has been referred to ever since the first industrial units were constructed (Jones, D. T., Woods, D. T., 1986, Microbiological. Reviews. 50(4), 484-524). The main cause of the low solvents titre is the toxicity of the final products and particularly of the butanol. A butanol concentration greater than 10-12 g/L in the culture medium is known to limit the growth of the strains of *Clostridium* (Zheng et al., 2009, J. Ind. Microb. & Biotechnol. 36:1127-1138).

Most scientific works carried out to date aim to improve the synthesis of butanol by the strains of *Clostridium*. To this end, several approaches have been applied in order to improve tolerance to butanol, including the approach based on mutagenesis and the selection of strains of *Clostridium* capable of resisting higher butanol contents (U.S. Pat. No. 4,757,010). The technique of random mutagenesis makes it possible to modify the gene pool of the strains in order to cause them to evolve towards a particular character by exerting environmental selection pressure. The technique optimizes and thus accelerates the phenomenon of natural selection.

Another technique that can be used is that of "genome shuffling" which makes it possible to combine and recombine the DNA of entire genomes of multiple organisms by imitating the reproductive process but on a larger scale. The phenomenon of recombination is carried out by the fusion of protoplasts of strains that have for example been selected following a mutagenic treatment and plating on a selective medium. Combination of the two techniques can help to obtain strains having an improved production of metabolites, better assimilation of the substrate, and greater tolerance to the products formed.

At present there is still a need for new bacterial strains which, cultured under suitable fermentation conditions, make it possible to obtain improved concentrations of a mixture of isopropanol and butanol.

SUMMARY OF THE INVENTION

The present invention relates to:

- a bacterium of the genus *Clostridium beijerinckii* deposited at the Institut Pasteur (CNCM, 25 rue du Docteur Roux, F-75724 PARIS Cedex 15, France) under No. CNCM I-4985 on 27 May 2015.
- a bacterium of the genus *Clostridium beijerinckii* deposited at the Institut Pasteur (CNCM, 25 rue du Docteur Roux, F-75724 PARIS Cedex 15, France) under No. CNCM I-4986 on 27 May 2015.
- a bacterium of the genus *Clostridium beijerinckii* deposited at the Institut Pasteur (CNCM, 25 rue du Docteur Roux, F-75724 PARIS Cedex 15, France) under No. CNCM I-4987 on 27 May 2015.
- a bacterium of the genus *Clostridium beijerinckii* deposited at the Institut Pasteur (CNCM, 25 rue du Docteur Roux, F-75724 PARIS Cedex 15, France) under No. CNCM I-5027 on 26 Nov. 2015.
- a bacterium of the genus *Clostridium beijerinckii* deposited at the Institut Pasteur (CNCM, 25 rue du Docteur Roux, F-75724 PARIS Cedex 15, France) under No. CNCM I-5028 on 26 Nov. 2015.
- a bacterium of the genus *Clostridium beijerinckii* deposited at the Institut Pasteur (CNCM, 25 rue du Docteur Roux, F-75724 PARIS Cedex 15, France) under No. CNCM I-5029 on 26 Nov. 2015.

The mutant bacteria CMCM I-4985, CNCM I-4986, CNCM I-4987 were obtained from the strain *Clostridium beijerinckii* DSMZ-6423 after treatment of the latter with a mutagenic agent, N-methyl-N'-nitro-N-nitrosoguanidine (NTG), and selection in a medium containing a significant quantity of isopropanol, or of methyl bromobutyrate or of ethyl bromobutyrate in order to select the mutants that are potentially useful for the production of a mixture of isopropanol and butanol. By comparison with the parent strain *Clostridium beijerinckii* DSMZ-6423, the selected bacteria have demonstrated a benefit in terms of final titre of the solvents Isopropanol and Butanol after fermentation of sugars.

The invention also relates to a mutant bacterium of the genus *Clostridium beijerinckii* deposited at the Institut Pasteur (CNCM, 25 rue du Docteur Roux, F-75724 PARIS Cedex 15, France) under No. CNCM I-4988 on 27 May 2015. The strain CNCM I-4988 originates from a step of genome shuffling carried out with the strains CNCM I-4986 and CNCM I-4987 followed by a step of selection based on the ability of the mutants to tolerate a significant concentration of isopropanol in its environment. The strain CNCM I-4988 utilized in fermentation has the ability to produce a mixture of solvents the isopropanol et butanol concentration of which is improved relative to the strain *Clostridium beijerinckii* DSMZ-6423.

The invention also relates to a process for the production of a mixture of isopropanol and butanol, by anaerobic fermentation carried out at a temperature comprised between 25 and 37° C., in a culture medium containing sugars using a bacterium selected from the bacteria CNCM I-4985, CNCM I-4986, CNCM I-4987 and CNCM I-4988.

The process according to the invention can also utilize a bacterium selected from the bacteria CNCM I-5027, CNCM I-5028 et CNCM I-5029. The bacteria CNCM I-5027, CNCM I-5028 and CNCM I-5029 were obtained by genome shuffling with strains mutated using the mutagenic agent NTG.

The culture medium preferably contains glucose as sugar.

According to an embodiment, the culture medium contains a hydrolyzed starch-containing substrate.

According to the invention, the culture medium can contain carboxylic acid. For example, the culture medium contains acetic acid and/or butyric acid.

DETAILED DESCRIPTION OF THE INVENTION

In order to improve the performances of the strain that naturally produces IBE, *Clostridium beijerinckii* DSMZ-6423, the inventors carried out a treatment with a mutagenic agent, N-methyl-N'-nitro-N-nitrosoguanidine (NTG), of said strain in order to modify its genetic content.

The mutagenesis technique used consists of bringing the mutagenic agent into contact with the bacterial strain in a liquid medium, then plating on different solid culture media, for example in Petri dishes, the strains originating from the treatment by the mutagen. The culture media comprise levels of isopropanol, or methyl bromobutyrate or ethyl bromobutyrate that are toxic to the native strain *Clostridium beijerinckii* DSMZ-6423.

The selection of the strains is based on the principle of searching for mutants resistant to isopropanol on the assumption that the latter would tolerate an accumulation of isopropanol during IBE fermentation tests.

The use of methyl bromobutyrate or ethyl bromobutyrate as a selection product is based on the article by Clark, S. W., Bennett, G. N., & Rudolph, F. B. ((1989). *Isolation and Characterization of Mutants of Clostridium acetobutylicum ATCC* 824 *Deficient in Acetoacetyl-Coenzyme A:Acetate/Butyrate:Coenzyme A-Transferase* (*EC* 2.8.3.9) *and in Other Solvent Pathway Enzymes. Appl. Environ. Microbiol.*, 55(4), 970-6) which describes mutants of *Clostridium acetobutylicum* ATCC824, selected for their resistance to 2-bromobutyrate, and which exhibit modified butyraldehyde et butanol dehydrogenase activities. The inventors assume that strains having a modified butyraldehyde activity can produce isopropanol in an improved manner, to the extent that the metabolic reactions involved in the ABE fermentation are similar to those of an IBE fermentation.

The mutated strains recovered after the culture step have thus had their genome modified in order to acquire a resistance to toxic products and potentially better fermentation capabilities for the production of solvents (more particularly isopropanol and butanol).

The resistant strains were then cultured in a growth medium containing glucose or a hydrolyzed starch-containing substrate in order to determine their actual ability to produce isopropanol and butanol. On completion of these fermentation steps, it was possible to select three mutant strains of *Clostridium beijerinckii* which were deposited, in accordance with the Budapest Treaty, at the Institut Pasteur (CNCM, 25 rue du Docteur Roux, F-75724 PARIS Cedex 15, France) on 27 May 2015, and which bear the references CNCM I-4985, CNCM I-4986 et CNCM I-4987 respectively.

According to the invention, a mutant strain CNCM I-4988 also deposited at the Institut Pasteur in accordance with the Budapest Treaty, was obtained by genome shuffling of mutant strains.

In order to initiate the shuffling step, fusions are induced between mutants of *Clostridium beijerinckii*. This genetic exchange between different populations thus mimics the recombinations characteristic of sexual reproduction. The daughter cells obtained after shuffling are again selected by searching for a change in their fermentation profiles. The “shuffling” process can be repeated over several generations (or rounds of shuffling) until a final strain is obtained, which is improved by its ability to produce solvents, isopropanol and butanol in particular, and to tolerate significant concentrations of isopropanol in its environment.

Thus the mutant strain CNCM I-4988 was obtained after a round of shuffling carried out with the mutant strains CNCM I-4986 et CNCM I-4987 and with a selection of strains for an improved tolerance to isopropanol (above 40 g/L of isopropanol).

The method of mutagenesis used in order to obtain the strains that form the subject of the invention is described in detail below.

The starting strain, also referred to by the term “wild-type”, is *Clostridium beijerinckii* DSMZ-6423 deposited at the Leibniz-Institut DSMZ—Deutsche Sammlung von Mikroorganismen and Zellkulturen GmbH.

The strain was precultured in a medium called GAPES, the composition of which is detailed in Table 1. The preculture step was carried out at a temperature of 35-37° C. over 24 hours.

TABLE 1

Composition of the GAPES medium

| Compound | Concentration (g/L) |
|---|---|
| Yeast extract | 2.5 |
| $KH_2PO_4$ | 1 |
| $K_2HPO_4$ | 0.6 |
| $MgSO_4$•$7H_2O$ | 1 |
| $FeSO_4$•$7H_2O$ | 0.0066 |
| p-Aminobenzoic acid | 0.1 |
| Ammonium acetate | 2.9 |
| Glucose | 60 |

This preculture is then used to initiate a culture in CGM medium (*Clostridium* Growth Medium), the composition of which is given in Table 2.

TABLE 2

| Composition of the CGM medium | |
|---|---|
| Compound | Concentration (g/L) |
| Yeast extract | 5 |
| $K_2HPO_4$ | 0.75 |
| $KH_2PO_4$ | 0.75 |
| $MgSO_4 \cdot 7H_2O$ | 0.4 |
| $MnSO_4 \cdot H_2O$ | 0.01 |
| $FeSO_4 \cdot 7H_2O$ | 0.01 |
| NaCl | 1 |
| Asparagine | 2 |
| $(NH_4)_2SO_4$ | 2 |
| Cysteine | 0.125 |
| Glucose | 12.5 |

Once cultured, the wild-type strain *Clostridium beijerinckii* DSMZ-6423 was subjected to different mutation conditions by contact, in a liquid CGM medium, with N-methyl-N'-nitro-N-nitrosoguanidine (NTG; Sigma-Aldrich) which is known for its mutagenic properties.

In a first test series, the wild-type strain of *Clostridium beijerinckii* DSMZ-6423 recovered in exponential growth phase, i.e. after being cultured for 3 to 4 hours, is brought into contact, at a temperature of 35-37° C. in a test tube, with NTG added to the CGM medium in order to obtain a concentration of 50 μg/mL of NTG. The contact with the NTG continues for 1 hour.

The cells are washed twice with a buffer solution of potassium phosphate (pH=6.6) before being taken up again in fresh CGM medium in order to carry out a step of regeneration of 1 to 3 h at 35° C. For the selection operation, the mutated cells are plated in selection dishes after the regeneration step. The selection medium is a CGM medium containing, as selection agent, ethyl bromobutyrate at a concentration of 0.5 mL/L. Incubation is carried out in the selection medium at a temperature of 35-37° C. over 24-48 hours. After being cultured for 24 to 48 hours, mutants exhibiting resistance to the selection agent were selected.

The performances of the different mutants thus selected were then tested in vials under anaerobic conditions and using two different fermentation media, namely the GAPES medium described in Table 1, and GAPES medium in which the glucose has been replaced with a hydrolyzed starch-containing substrate (GRITZ) corresponding to a concentration of 70 g/L glucose equivalent in said medium.

The anaerobic fermentations are carried out at a temperature of 37° C. over 48 hours under stirring.

In a second test series, the wild-type strain of *Clostridium beijerinckii* DSMZ-6423 is cultured in CGM medium and collected in exponential phase, i.e. after being cultured for 3 to 4 hours, and is then brought into contact with 75 μg/mL of NTG. The mutants were then selected under the same conditions as mentioned above, but using isopropanol at a concentration of 40 g/L as selection agent.

The mutants thus selected, which have acquired a resistance to isopropanol, are then tested in fermentation under anaerobic conditions in vials, in the medium described in Table 1 and also in GAPES medium to which, instead of glucose, a hydrolyzed starch-containing substrate (GRITZ) has been added in order to provide 70 g/L of glucose equivalent. The anaerobic fermentations are carried out over 48 hours at a temperature of 37° C. under stirring.

In a third test series, the wild-type strain of *Clostridium beijerinckii* DSMZ-6423 is cultured in the CGM medium and collected in exponential phase, i.e. after being cultured for 3 to 4 hours, and is then brought into contact with 50 μg/mL of NTG. The mutants are selected using a culture solution of CGM also containing 40 g/L of isopropanol.

The mutants resistant to isopropanol are then tested in fermentation under anaerobic conditions in vials, in the medium described in Table 1 and also in GAPES medium containing, instead of glucose, the hydrolyzed starch-containing substrate (GRITZ) providing 70 g/L of glucose equivalent. The anaerobic fermentations are carried out over 48 hours at a temperature of 37° C. and under stirring.

Table 3 below summarizes the results of analysis of the solvents produced after 48 hours of anaerobic fermentation in GAPES medium.

The solvents are assayed by gas chromatography (Varian® device), with a CP-PoraBOND Q column and an FID (Flame Ionization Detector). Propan-1-ol is used as an internal standard.

The chromatography parameters are as follows:

Column: length 25 meters; internal diameter (ID): 0.32 mm; external diameter (ED): 0.45 mm; thickness of the film: 5 μL Temperature of the injector: from 90° C. to 250° C., 150° C./min Flow rate of the carrier gas: 1.6 mL/min (6.8 psi)

Temperature of the column: from 50° C. to 250° C., 50° C./min

Temperature of the FID detector: 80° C.

Injection volume: 1 μL

TABLE 3

Concentration of solvents after fermentation in GAPES medium from mutant strains obtained by random mutagenesis using NTG.

| *C. beijerinckii* DSMZ 6423 | | Ethanol | Acetone | | |
|---|---|---|---|---|---|
| Concentration of NTG/ | | Isopropanol | Butanol | | |
| | | [Solvent] in g/L | | | |
| Selection medium | Strain No. | 0.1 | 0.1 | 2.4 | 7.3 |
| 50 μg/mL of NTG/ | 6 | 0.1 | 0.1 | 2.8 | 7.2 |
| Selection medium | 7 | 0.2 | 0.1 | 2.5 | 7.1 |
| containing ethyl | 8 | 0.1 | 0 | 2.4 | 7 |
| bromobutyrate at | 9* | 0.2 | 0 | 2.8 | 10.5 |
| 0.5 mL/L | 10 | 0.1 | 0.1 | 2.4 | 7.2 |
| NTG 75 μg/mL/ | 1 | 0.2 | 0.1 | 2.8 | 8.3 |
| Selection medium | 3 | 0.2 | 0 | 0.3 | 6.6 |
| containing | 5 | 0.1 | 0 | 1.9 | 5.3 |
| isopropanol at | 6* | 0.1 | 0.1 | 2.3 | 5.5 |
| 40 g/L | 7 | 0.1 | 0.1 | 1.9 | 7.8 |
| | 8 | 0.1 | 0 | 0.6 | 0.7 |
| | 9 | 0.1 | 0 | 2.3 | 6.5 |
| | 10 | 0.1 | 0 | 2.2 | 6.2 |
| NTG 50 μg/mL/ | 1 | 0.1 | 0.1 | 2.5 | 7.1 |
| Selection medium | 2 | 0.1 | 0 | 2.3 | 6.6 |
| containing | 3 | 0.1 | 0.1 | 2.7 | 6.4 |
| isopropanol at | 4 | 0.4 | 0.1 | 2.4 | 7 |
| 40 g/L | 5 | 0.1 | 0 | 1.9 | 6.5 |
| | 6 | 0.2 | 0 | 2.4 | 7.3 |
| | 7* | 0 | 0 | 3.9 | 9.3 |

The mutant strains which have been deposited according to the Budapest Treaty are indicated in Table 3 by an asterisk.

Strain 9* corresponds to the strain CNCM I-4985 deposited at the Institut Pasteur (CNCM, 25 rue du Docteur Roux, F-75724 PARIS Cedex 15, France) on 27 May 2015.

Strain 6* corresponds to the strain CNCM I-4986 deposited at the Institut Pasteur (CNCM, 25 rue du Docteur Roux, F-75724 PARIS Cedex 15, France) on 27 May 2015.

Strain 7* corresponds to the strain CNCM I-4987 deposited at the Institut Pasteur (CNCM, 25 rue du Docteur Roux, F-75724 PARIS Cedex 15, France) on 27 May 2015.

Table 4 gives the concentrations of solvents produced using the mutant strains of *Clostridium beijerinckii* CNCM I-4985, CNCM I-4986 and CNCM I-4987 by fermentation in GAPES medium in which the glucose has been replaced by a hydrolyzed starch-containing substrate (GRITZ) at 70 g/L of glucose equivalent.

After anaerobic fermentation for 48 hours, the glucose contents are determined by HPLC (Varian®) with an Aminex®HPX-87P column (Biorad, 300 mm in length and 7.8 mm in diameter) at 80° C. The eluent used is water with a flow rate of 0.4 mL/min. The detector is a refractometer (Varian® 350 RI). The volume of sample injected is 35 μL.

The solvents are analyzed by gas chromatography as mentioned above.

TABLE 4

Concentration of solvents after fermentation in GAPES medium containing a hydrolyzed starch-containing substrate (GRITZ) (70 g/L glucose equivalent) replacing the glucose.

| | Concentration (g/L) | | | | | | | | Yield |
|---|---|---|---|---|---|---|---|---|---|
| | Glucose consumed | Acetate consumed | Butyrate | Ethanol | Acetone | Isopropanol | Butanol | Total solvent | Solvent/ Glucose |
| Strain DSMZ 6423 | 44.8 | 3.1 | 3.1 | 0.18 | 0.17 | 6 | 10.1 | 16.4 | 36.7% |
| Strain CNCM I-4985 | 47.9 | 4.4 | 1.7 | 0.23 | 0.21 | 7.1 | 10.4 | 18 | 37.5% |
| Strain CNCM I-4986 | 48.1 | 4.5 | 1.7 | 0.21 | 0.16 | 7 | 10.3 | 17.7 | 36.9% |
| Strain CNCM I-4987 | 47.3 | 4 | 1.9 | 0.2 | 0.2 | 6.3 | 10.6 | 17.3 | 36.6% |

It is noted that the fermentation carried out with the strains CNCM I-4985, CNCM I-4986 and CNCM I-4987 produce a fermentation must having higher concentrations of isopropanol and butanol than that produced by the wild-type strain *Clostridium beijerinckii* DSMZ 6423.

The mutant strains obtained after the step of random mutagenesis with NTG and selection for their resistance to isopropanol at 40 g/L or to ethyl bromobutyrate at 0.5 mL/L, were used for a genome shuffling step according to the protocol described by Gao, X., Zhao, H., Zhang, G., He, K. & Jin, Y. (2012). *Genome shuffling of Clostridium acetobutylicum CICC* 8012 *for improved production of acetone-butanol-ethanol* (*ABE*). *Curr. Microbiol.,* 65(2), 128-32.

The mutant strains are first introduced separately, in the exponential phase, into CGM medium and collected after being cultured for 3 to 4 hours. The cultures are then centrifuged for 10 minutes at 4000 G and washed twice with a solution of sodium maleate monohydrate No. 1 (SMM 1) at pH 6.5 containing 0.5 M of sucrose, 20 mM of sodium maleate monohydrate, and 20 mM of $MgCl_2$.

The collected cells are brought into contact, at 35° C. for 1 h, with a solution of sodium maleate monohydrate No. 2 which has the following composition: 0.5 M of sucrose, 20 mM of sodium maleate monohydrate, 20 mM of $MgCl_2$, 1 g/L of cysteine, 1 g/L of glutathione to which 15 mg/mL of lysozyme has been added. On completion of the treatment, the cells are collected, washed with the solution of sodium maleate monohydrate No. 1 and centrifuged at 4000 G for 5 min.

The different populations are then mixed in 10 mL of a solution of sodium maleate monohydrate No. 3 (0.5 M of sucrose, 20 mM of sodium maleate monohydrate, 20 mM of $MgCl_2$, 1 g/L of cysteine, 1 g/L of glutathione, 50 mM $CaCl_2$) to which 30% w/v (30 g per 100 mL) of PEG 4000 has been added and incubated for 20 min at a temperature of 35-37° C. in order to induce fusion between protoplasts. The fused cells are suspended in CGM medium and regenerated on CGM agar over 40 hours. Several crossings by protoplast fusion were carried out from mutant strains treated with NTG. The genetically shuffled strains were then selected for an increased tolerance to isopropanol in CGM medium (from 45 to 50 g/L of isopropanol).

Table 5 compares the solvent concentrations of the fermentation must, after fermentation for 48 hours, obtained with the strain CNCM I-4988 deposited at the Institut Pasteur (CNCM, 25 rue du Docteur Roux, F-75724 PARIS Cedex 15, France) on 27 May 2015 and the wild-type strain *Clostridium beijerinckii* DSMZ 6423. The fermentations were carried out in GAPES medium containing hydrolyzed starch-containing substrate (GRITZ; 70 g/L glucose equivalent) replacing the glucose. The strain CNCM I-4988 originates from a single round of genome shuffling with the strains CNCM I-4986 and CNCM I-4987.

TABLE 5

Concentration of solvents after fermentation in GAPES medium containing a hydrolyzed starch-containing substrate (GRITZ; 70 g/L glucose equivalent) replacing the glucose.

| | Concentration (in g/L) | | | | | | | | Yield |
|---|---|---|---|---|---|---|---|---|---|
| | Glucose consumed | Acetate consumed | Butyrate | Ethanol | Acetone | Isopropanol | Butanol | Total solvent | Solvent/ Glucose |
| Strain DSMZ 6423 | 44.8 | 3.1 | 3.1 | 0.18 | 0.17 | 6 | 10.1 | 16.4 | 36.7% |
| Strain CNCM I-4988 | 45.9 | 3.5 | 0.8 | 0.21 | 0.21 | 6 | 10.7 | 17.2 | 37.4% |

It is noted that the strain CNCM I-4988 produces more butanol than the wild-type strain, while maintaining an identical isopropanol production level.

Different mutant strains were also obtained after two rounds of genome shuffling, and were then tested afterwards in anaerobic fermentation in a GAPES medium to which a hydrolyzed starch-containing substrate (70 g/L glucose equivalent) had been added, replacing the glucose.

The strain CNCM I-5027 was isolated as described below.

A step of genome shuffling was carried out with the strain CNCM I-4985 and with a strain originating from mutagenesis with a solution of NTG at 75 μg/mL then selected for its resistance to a CGM medium containing 40 g/L of isopropanol. After the round of shuffling, mutated cells were selected using a CGM selection medium containing 40 g/L of isopropanol. Incubation in the selection medium is carried out at a temperature of 35-37° C. and over 24 hours. After being cultured for 24 hours, mutants exhibiting resistance were selected and again subjected to an incubation at a temperature of 35-37° C. and for 24 hours in a CGM medium containing 50 g/L of isopropanol. The strain CNCM I-5027 is the result of this second selection step.

As regards the strain CNCM I-5028, it is the result of a step of genome shuffling carried out with the strain CNCM I-4985 and with two other strains which have been subjected to a prior step of mutagenesis with NTG (75 μg/mL) selected in a CGM selection medium containing 40 g/L of isopropanol. As above, the strain CNCM I-5028 originates from two selection steps utilizing a CGM selection medium containing 40 g/L of isopropanol, then a CGM selection medium containing 50 g/L of isopropanol.

The strain CNCM I-5029 was isolated by applying the protocol described above but in which the step of genome shuffling was carried out with two strains originating from mutagenesis with NTG (75 μm/mL) and selected for their resistance in a CGM selection medium containing 40 g/L of isopropanol. As previously, isolation of the strain CNCM I-5029 was carried out in two steps utilizing a CGM medium containing 40 g/L of isopropanol then a CGM selection medium containing 50 g/L of isopropanol.

Table 6 gives the solvent concentrations of the fermentation must after fermentation for 48 hours at 37° C., obtained with the strains CNCM I-5027, CNCM I-5028 and CNCM I-5029. The fermentations were carried out in GAPES medium, the composition of which is given in Table 1.

TABLE 6

Concentration of solvents after fermentation at 37° C. in GAPES medium containing a hydrolyzed starch-containing substrate (GRITZ; 70 g/L glucose equivalent) replacing the glucose.
Concentration (in g/L)

| | Glucose consumed | Butyrate | Ethanol | Acetone | Isopropanol | Butanol | Yield Solvent/ Glucose |
|---|---|---|---|---|---|---|---|
| Strain DSMZ 6423 | 18 | 0.77 | 0.24 | 0.09 | 1.54 | 5.69 | 42% |
| CNCM I-5027 | 23 | 0.99 | 0.22 | 0.07 | 1.59 | 4.69 | 29% |
| CNCM I-5028 | 21 | 0.60 | 0.19 | 0.06 | 1.9 | 5.75 | 38% |
| CNCM I-5029 | 22 | 0.66 | 0.22 | 0.08 | 1.81 | 6.24 | 38% |

It is observed that the strains CNCM I-5027, CNCM I-5028 and CNCM I-5029 are capable of producing more isopropanol than the reference strain DSM 6423. Moreover, CNCM I-5028 and CNCM I-5029 make it possible to produce more butanol relative to the strain DSMZ 6423.

The invention claimed is:

1. A bacterium selected from the group consisting of a bacterium of the genus *Clostridium beijerinckii* deposited at the Institut Pasteur (CNCM, 25 rue du Docteur Roux, F-75724 PARIS Cedex 15, France) under No. CNCM 1-4985 on 27 May 2015;

bacterium of the genus *Clostridium beijerinckii* deposited at the Institut Pasteur (CNCM, 25 rue du Docteur Roux, F-75724 PARIS Cedex 15, France) under No. CNCM 1-4986 on 27 May 2015;

bacterium of the genus *Clostridium beijerinckii* deposited at the Institut Pasteur (CNCM, 25 rue du Docteur Roux, F-75724 PARIS Cedex 15, France) under No. CNCM 1-4987 on 27 May 2015;

bacterium of the genus *Clostridium beijerinckii* deposited at the Institut Pasteur (CNCM, 25 rue du Docteur Roux, F-75724 PARIS Cedex 15, France) under No. CNCM 1-4988 on 27 May 2015;

bacterium of the genus *Clostridium beijerinckii* deposited at the Institut Pasteur (CNCM, 25 rue du Docteur Roux, F-75724 PARIS Cedex 15, France) under No. CNCM 1-5027 on 26 Nov. 2015;

bacterium of the genus *Clostridium beijerinckii* deposited at the Institut Pasteur (CNCM, 25 rue du Docteur Roux, F-75724 PARIS Cedex 15, France) under No. CNCM 1-5028 on 26 Nov. 2015; and bacterium of the genus *Clostridium beijerinckii* deposited at the Institut Pasteur (CNCM, 25 rue du Docteur Roux, F-75724 PARIS Cedex 15, France) under No. CNCM 1-5029 on 26 Nov. 2015.

2. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-4986 on 27 May 2015.

3. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-4987 on 27 May 2015.

4. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-4988 on 27 May 2015.

5. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-5027 on 26 Nov. 2015.

6. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-5028 on 26 Nov. 2015.

7. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-5029 on 26 Nov. 2015.

8. A process for the production of a mixture of isopropanol and butanol, comprising anaerobic fermentation of a culture medium containing sugars, at a temperature comprised between 25 and 37° C., by a bacterium according to claim 1.

9. Process according to claim 8, wherein the sugars of the culture medium are glucose.

10. Process according to claim 8, wherein the culture medium contains a hydrolyzed starch-containing substrate.

11. Process according to claim 8, wherein the culture medium contains carboxylic acid.

12. Process according to claim 11, wherein the carboxylic acid medium is acetic acid or butyric acid.

13. A bacterium according to claim 1, which is the bacterium of the genus *Clostridium beijerinckii* deposited at the Institut Pasteur (CNCM, 25 rue du Docteur Roux, F-75724 PARIS Cedex 15, France) under No. CNCM 1-4985 on 27 May 2015.

* * * * *